United States Patent
Charlot

(10) Patent No.: US 9,873,129 B1
(45) Date of Patent: Jan. 23, 2018

(54) MULTI-PLANAR MICROELECTRODE ARRAY DEVICE AND METHODS OF MAKING AND USING SAME

(71) Applicant: Charlot Biosciences, Inc., San Diego, CA (US)

(72) Inventor: David Jean Charlot, San Diego, CA (US)

(*) Notice: Subject to any disclaimer, the term of this patent is extended or adjusted under 35 U.S.C. 154(b) by 0 days.

(21) Appl. No.: 15/383,343

(22) Filed: Dec. 19, 2016

(51) Int. Cl.
  *G01N 27/447* (2006.01)
  *G01N 27/453* (2006.01)
  *B03C 5/02* (2006.01)
  *G01N 15/06* (2006.01)
  *G01N 27/04* (2006.01)

(52) U.S. Cl.
  CPC ......... *B03C 5/026* (2013.01); *G01N 15/0656* (2013.01); *G01N 27/045* (2013.01); *G01N 27/44756* (2013.01)

(58) Field of Classification Search
  CPC .......................................... B03C 5/00–5/028
  See application file for complete search history.

(56) References Cited

U.S. PATENT DOCUMENTS

| | | | | |
|---|---|---|---|---|
| 5,653,859 | A | * | 8/1997 | Parton ...................... B03C 5/028 204/450 |
| 5,989,402 | A | * | 11/1999 | Chow .................. B01J 19/0093 204/450 |
| 7,635,420 | B1 | | 12/2009 | Li et al. |
| 2003/0157587 | A1 | * | 8/2003 | Gomez ............ G01N 33/56911 435/30 |
| 2014/0367260 | A1 | * | 12/2014 | Dickerson ............... B03C 5/005 204/547 |
| 2015/0283553 | A1 | * | 10/2015 | Charlot ................... B03C 5/005 204/547 |

OTHER PUBLICATIONS

W. Michael Arnold, "Dielectrophoretic Cell Separation: Some Hints and Kinks," Proc. ESA Annual Meeting on Electrostatics 2010.*
Chang et al., "Electrical characterization of micro-organisms using microfabricated devices," J. Vac. Sci. Technol. B 20(5), Sep./Oct. 2002.*
Buyong et al. "A Tapered Aluminium Microeletrode Array for Improvement of Dielectrophoresis-Based Particle Manipulation." (2015) Sensors 15:10973-10990.
Salari et al. "A novel alternating current multiple array electrothermal micropump for lab-on-a-chip applications." (2015) Biomicrofluids 9:014113.
Hawkings et al. "Electrothermal flow effects in insulating (electrodeless) dielectrophoresis systems." (2010) Electrophoresis 31:3622-3633.
Sasaki "Recent Applications of AC Electrokinetics in Biomolecular Analysis on Microfluidis Devices." (Jan. 2012) Analytical Sciences 28:3-8.

* cited by examiner

*Primary Examiner* — Alexander Noguerola
(74) *Attorney, Agent, or Firm* — Lewis Kohn & Walker LLP; David M. Kohn

(57) ABSTRACT

The present invention provides for microelectrode array devices and method of making and using same for the purpose of isolating and analyzing micro- and nanoparticles contained within a fluid solution. In various aspects, the present invention is designed to take advantage of electrokinetics and the separation of certain forces in order to influence and control small particles in a fluid solution, thereby allowing further analysis to be conducted on such particles.

17 Claims, 14 Drawing Sheets

MULTI-PLANAR MICROELECTRODE ARRAY DEVICE AND METHODS OF MAKING AND USING SAME

FIELD OF THE INVENTION

This application relates generally to the field of devices utilizing electrokinetics within a platform device to influence and control particle motion in fluids. Specifically, this application allows for quantification or recovery of particles based on their inherent properties.

BACKGROUND OF THE INVENTION

Experimental design in the field of molecular diagnostics have evolved at an incredible rate over the last two decades. Analyses which historically took weeks or months to complete can now be completed within a day, resulting in a substantial savings of both time and costs. In addition to these spectacular advantages, the technology has progressed in another important parameter, which is one of scale. Through an improved understanding of electrochemistry, thermodynamics and physics, technicians have now achieved the capacity to isolate and observe particles at the nanoscale, and beyond.

Typically, a given biological sample must be thoroughly prepared prior to analysis, with such preparation being burdensome and, in a worst case scenario, unintentionally affecting the integrity of the sample to be analyzed. For example, many diagnostic assays on clinical samples containing biological components, such as blood, tissue or cells, require separation of the particles of interest from the crude sample by disrupting or lysing the cells to release such molecules including proteins and nucleic acids of interest, followed by purification of such proteins and/or nucleic acids. Only after the completion of such processing steps can analysis of the molecules of interest be initiated.

It is well known that certain forces may be applied to a sample in solution during processing in order to separate such sample into its component parts. One of the forces is known as dielectrophoresis (DEP) and is particularly useful once the experimental scale is performed in the micro- or nanoscale range, or if cells are utilized in the sample. DEP occurs when a polarizable particle is suspended or subjected to a non-uniform electric field (Kirby, B J, Micro- and Nanoscale Fluid Mechanics: Transport in Microfluidic Devices, Cambridge Univ Press (2010)). All particles exhibit some DEP activity in the presence of a non-uniform electric field, with the strength of such DEP force being highly correlated with several factors including, among others, the size, shape and electrical properties of the particles, frequency of the electric field and the solution in which the sample particles are being examined. Subjecting particles in solution to an electric field, where the electric field is set at a particular frequency, allows for specific and selective processing of the particles in solution, thereby allowing for very precise measurements to be obtained from the particles.

Prior art devices utilizing DEP forces to isolate and examine particles at the microscale are well known. Such devices include use of a glass slide having exposed electrodes plated on the slide surface, across which microliter quantities of fluid flows containing particles for analysis. These particles range from cells or proteins to nucleic acids, with such particles being capable of separation using DEP forces based on each particle's respective dielectric properties through use of separation buffers having specific conductivity and an external current (AC signal) having an appropriate amplitude and frequency.

These prior art devices, however, come with various problems, including binding of particles to exposed portions of the glass surface and, at times, the electrodes themselves. Additionally, the surfaces and electrodes of such prior art devices are quite small, resulting in the potential of aggregates of even the smallest of particles interfering with fluid flow and blocking certain processing steps between wash cycles.

The above mentioned prior art devices are based on microchip arrays attempting to take measurements of microliter quantities. There are macro-scale devices that have employed high voltage DC pulses in order to separate and analyze proteins and nucleic acids. While such devices generally overcome the blockage limitations of microscale arrays on a chip, the macroscale devices come with their own set of unique disadvantages. For example, some commercial macroscale devices use lysis conditions that limit the molecular weight of nucleic acids allowed for passage through pores created in the cell membranes. Additionally, released nucleic acids are often lost due to their non-specific binding to the surface of the lysis chamber. Furthermore, most macroscale devices require the use of a membrane or hydrogel which sits between the solution and electrodes, resulting in further limitations to such devices.

Most advanced devices in the prior art have attempted to take advantage of the various phenomena found within the field of electrokinetics relative to microfluidics. Electrokinetics describes the combination of DEP, electro thermal flow (ETF), electro osmotic flow (EOF) and other forces acting on particles found in a fluid as a function of frequency and amplitude of an applied electric field. One limitation found within even the most sophisticated devices in the prior art is the requirement that the DEP/ETF/EOF forces be coupled to one another. Other limitations include a restricted geometric configuration of electrode arrays based on a two-lead system, an inability to overcome the frequency and amplitude limitations found within high salinity systems (such as biological fluids) and poor processing of fluids as the salinity levels decrease to that of deionized water.

There is a frequency (less than 30 kHz) and amplitude (less than 20 Vpp) limit to capturing particles using electrokinetics in fluids with a conductivity greater than 1 mS/cm.

The frequency limit reduces the amount of mixing possible in the solution. As a result, there is an exponential decrease in the available concentration of particles present in the DEP depletion zone as a function of time. The DEP depletion zone is where particles can be influenced by the DEP force. This exponential decrease in concentration negatively influences capture efficiency of the devices exploiting electrokinetics for particle isolation, quantification, and recovery.

The amplitude limit reduces the potential DEP trapping force because at low frequencies electrode destruction is caused by electrolysis (strong changes in pH at the electrode locations) and destroys the electrodes, thereby removing their ability to function. The strong changes in pH can also cause changes to particles able to be captured by either altering their native state or destroying them. The amplitude limit is also required to balance the ability for the DEP forces to counter act the flow forces generated by ETF and EOF. As voltage (V) increases, DEP force increases as a function of $V'$ whereas flow forces increase as a function of $V^4$ or $V^5$ depending on fluid conductivity (Loire et al., A theoretical and experimental study of ac electrothermal flows, J. Phys.

D: Appl. Phys., 45: 185301 (2012); Hong et al., Numerical simulation of AC electrothermal micropump using a fully coupled model, Microfluid Nanofluid, 13: 411-420 (2012)).

There is a limit to the amount of mixing that is possible in fluids with conductivity lower than 1 mS/cm generated by electro thermal flow due to a large reduction in Joule heating. This also limits the available concentration of particles in the DEP depletion zone. Increasing the amplitude of the electric field helps to increase the effective size of the DEP depletion zone, but this has a limit due to the generation of electrolysis.

There remains a need in the art for macroscale devices capable of sample processing down to the nanoscale level, while resolving the limitations described above.

SUMMARY OF THE INVENTION

The present invention provides a novel microelectrode array device constructed in a way to resolve the frequency and amplitude limitations through decoupling of DEP from ETF and EOF forces. In alternate embodiments, the present invention provides for a microelectrode array device that alters a gradient of an electric field surrounding at least one electrode relative to at least one adjacent electrode, wherein the electrode arrangement is configured using three or more separate input signals to independently operate at least three different polarity configurations at any given time. In a preferred embodiment, there are at least three separate input signals delivered to the electrode arrangement, resulting in at least three different charge configurations applied to each electrode.

In one aspect, the present invention provides for a microelectrode array device comprising a substrate further comprising a plurality of electrodes arranged in a geometric pattern, the plurality of electrodes deposited using a means selected from the group consisting of photolithography, vapor deposition, sputtering, screen printing, three dimensional (3D) printing and electroplating. Preferably, the substrate is composed of at least one of glass, silicon or a nonconductive polymer.

In another aspect, the plurality of electrodes are made of metal or a non-metallic conductive material. Preferably, the thickness of the electrodes of the present invention is from about 10 nm to about 10 In another aspect, the electrodes are configured to enable insulated and non-insulated electric fields. Alternatively, the electrode arrangement consists of insulated electrodes and non-insulated electrodes. Most preferably, the electrode configuration is geometrically arranged to facilitate the decoupling of the DEP forces from those forces derived from ET and EO flow. Alternatively, the electrodes can be circular in shape with angle of orientation between adjacent electrodes ranging from about 0 to about 90 degrees.

Another alternative embodiment of the methods and devices of the present invention include a microelectrode array device capable of handling up to about 3 amps (3 A) to power the electrode configuration. Minimally, individual electrodes are configured to accommodate up to about 0.1 A or 100 milliamps (100 mA).

In another aspect, the present invention provides for a microelectrode array device comprising at least three independent electrodes, wherein each electrode may carry a charge that is positive (+), negative (−) or neutral.

In yet another aspect, there are at least two different planes in a Z-dimension between independent and adjacent electrodes to impact the non-uniformity of the electric field across the electrode arrangement. Furthermore, the Z dimension between independent electrodes can vary from at least 1 nm to more than 5 nm. Preferably, each electrode in the electrode arrangement has independent yaw, pitch and roll with respect to each other.

In certain embodiments, the microelectrode array devices described herein comprise multi-planar floating electrodes within the dielectric substrate, wherein the floating electrodes are not connected to any power source.

In other aspects, the devices of the present invention provide for an impedance bridge circuit between electrodes to modulate capacitance with the substrate. Additionally, there are cavities within the substrate to generate temperature gradients throughout the device in the presence of an electric field, wherein the form of the cavities are pits or valleys within the substrate.

In another aspect, the devices of the present invention further provide a dielectric passivation layer to cover deposited electrode material and selectively expose certain regions of each electrode within the array.

In another aspect, the devices of the present invention further provide a swellable or non-swellable porous dielectric passivation layer to cover deposited exposed electrodes material. This dielectric passivation layer enables water molecules to pass through to and make contact with the exposed electrodes.

In another preferred aspect, the microelectrode array devices described herein further comprise a field effect transistor to enable quantification of particles influenced by the electric field and electrode performance. Preferably, the device comprises at least one field effect transistor per exposed electrode. In another embodiment, the microelectrode array device comprises impedance sensors capable of quantifying particles in solution influenced by the electric field. Preferably, the device comprises at least one impedance sensor per exposed electrode.

In yet another aspect, the present invention further provides for a fluidic chamber that contains a solution directly over the electrode arrangement, wherein the fluidic chamber comprises channels capable of expanding or collapsing based on at least one stimulus.

In a preferred embodiment, the present invention provides for methods of manufacturing a microelectrode array device comprising providing a device comprising non-flat, planar structures, wherein the structures are configured to facilitate electrokinetic phenomena, further wherein the device is created using a technique selected from the group consisting of 3D printing, screen printing, laser sintering, laser ablation and MEMS photolithography.

Preferably, the microelectrode array devices of the present invention are capable of generating a non-uniform electric field when sourced with a current signal selected from the group consisting of an alternating current, direct current and pulsed direct current. The current signal is in a waveform selected from the group consisting of sine, square, triangle, continuous and any combination of the above.

In a preferred embodiment, the devices of the present invention are capable of processing fluid solutions with conductivity ranging from about 0 Siemen/meter (S/m) to about 5 S/m, from about 0 S/cm to about 0.05 S/cm or from about 0 mS/cm to about 50 mS/cm. Optionally, sample fluids may comprise deionized water, physiological fluids or brackish water, with viscosity of the sample fluid ranging from about 1 centiPoise (cP) to about 100 cP and from about 0.001 Pascal second to about 0.1 Pascal second. Preferably, the devices of the present invention are capable of influencing particles ranging from about 10 nm to about 50,000 nm and from about 0.01 microns (μm) to about 50 μm. Particles can include cellular and subcellular particles, as well as synthetic particles selected from the group consisting of dextrans, polystyrene microspheres, polystyrene nanospheres and other polymers.

Preferably, the devices of the present invention provide for microelectrode array devices capable of generating a dielectrophoretic high field region and low field region, wherein each region is selectively determined based on electric field strength and specific geometry of electrode arrangement, wherein the electrodes are further comprised of insulated electrodes and non-insulated electrodes. Optionally, the devices of the present invention are capable of generating ETF and EOF forces. Most preferably, the microelectrode array devices of the present invention use the uncoupling of the DEP and ETF/EOF forces in order to separate particles based on specific effective stokes radius and dielectric properties of each particle within a fluid.

In yet another embodiment, the present invention provides for microelectrode array devices configured to quantify at least one particle in a solution comprising (1) providing a non-uniform electric field; (2) measuring a change in current or impedance using field effect transistor at a time point selected from the group consisting of real-time, during or after the at least one particle influenced by the non-uniform electric field (i) enters a dielectrophoretic depletion zone, (ii) is immobilized in a dielectrophoretic high field region or low field region or (iii) is released in the dielectrophoretic high field region or low field region, respectively. Optionally, the microelectrode array devices are configured to quantify at least one particle in a solution comprising (1) providing a non-uniform electric field; and (2) measuring a change in impedance using electrical impedance tomography (EIT) or impedance spectroscopy at a time point selected from the group consisting of real-time, during or after the at least one particle influenced by a non-uniform electric field (a) enters a dielectrophoretic depletion zone, (b) is immobilized in a dielectrophoretic high field region or low field region or (c) is released in the dielectrophoretic high field region or low field region, respectively. In another aspect, the microelectrode array devices are configured to quantify at least one particle in a solution comprising (1) providing a non-uniform electric field; and (2) measuring a change in fluorescence using optical microscopy at a time point selected from the group consisting of real-time, during or after the at least one particle influenced by a non-uniform electric field (a) enters a dielectrophoretic depletion zone, (b) is immobilized in a dielectrophoretic high field region or low field region or (c) is released in the dielectrophoretic high field region or low field region, respectively.

In another aspect, the microelectrode array devices of the present invention provide for a plurality of electric input signals to operate the electrode arrangement contained within each device, the electric input signal is at least one selected from the group consisting of a sine, square and triangle waveform. Preferably, the electrode arrangement comprise independence electrodes capable of being set to a charge selected from the group consisting of a positive (+), negative (−) and neutral charge.

BRIEF DESCRIPTION OF THE DRAWINGS

The novel features of the present invention are set forth herein embodied in the form of the claims of the invention. Features and advantages of the present invention may be best understood by reference to the following detailed description of the invention, setting forth illustrative embodiments and preferred features of the invention, as well as the accompanying drawings, of which:

DETAILED DESCRIPTION OF THE INVENTION

Definitions

Figure 1A:
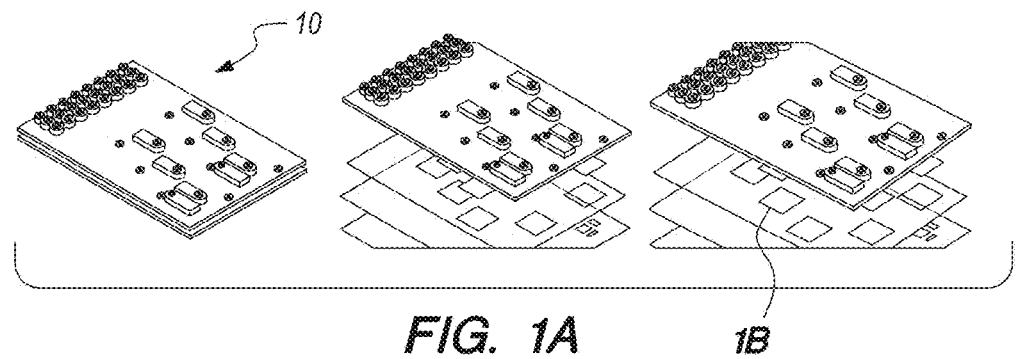
FIGS. 1A-1C show views of one embodiment of the device of the present invention. (A) an exploded of a preferred fabrication embodiment of the microelectrode devices of the present invention consisting of layers; (B) is a magnified view of the cartridge element of the present invention; (C) is a further magnified view of the cartridge element which details the microelectrode array embedded within the cartridge.

As used herein, the term "dielectrophoresis" or "DEP" refers to a phenomenon in which a force is exerted on a dielectric particle in the presence of an electric field. The particle does not have to contain any particular charge and the electric field may be non-uniform. While all particles exhibit dielectrophoretic activity in the presence of electric fields, the strength of the DEP force depends on a number of variables, including physical properties of the particle to be measured, as well as certain parameters of the electric field surrounding the particle. The time-averaged DEP force is expressed by:

$$\langle F_{DEP} \rangle = 2\pi \in_m r^3 Re(\beta) \nabla E_{rms}^2$$

$E_{rms}$ is the root mean square (rms) of the electric field. $Re(\beta)$, theoretically ranging from −0.5 to 1, represents the real part of the Clausius Mossotti (CM) factor and is expressed as:

$$\beta = \frac{\varepsilon_p - \varepsilon_m}{\varepsilon_p + 2\varepsilon_m}$$

As used herein, the term "electro thermal flow", "ETF" or "ET flow" refers to an electrokinetic force present at the sub-micron scale where buoyancy has a diminished influence and where high field gradients are possible in low voltage conditions. ETF is useful in higher conductivity fluids and arises from Joule heating of a fluid in a microfluidic device with an applied AC potential. Where temperature-dependent conductivity is present through Joule heating of a fluid, such interactions, within an applied electric field inside a microfluidic device, results in fluid motion in the form of a predictable, circulating pattern. The force due to electrothermal flow is expressed as:

$$\langle F_{ET} \rangle = \frac{1}{2} Re \left[ \frac{\varepsilon_m (a \cdot b)}{1 + \left( \frac{\omega \varepsilon_m}{\sigma_m} \right)^2} (\nabla T \cdot E) E - \frac{1}{4} \varepsilon_m a E^2 \nabla T \right]$$

As used herein, the term "electro osmotic flow", "EOF" or "EO flow" refers to the motion of a liquid induced by an applied potential across a microchannel, or any other fluid conduit. EOF is particularly useful in microfluidic devices, which involve systems containing highly charged surfaces, which enables electric fields to assist in particle separation according to electroosmotic flow rates (Morgan, H., & Green, N. G., *AC electrokinetics: Colloids and nanoparticles.* Baldock, Hertfordshire, England: Research Studies Press (2003)).

As used herein, the term "microelectrode array device" refers to a device comprising a geometric arrangement of a plurality of electrodes, contained within a suitable substrate, in order to isolate particles within a fluid solution.

Described herein are methods, devices and systems specifically configured to process, quantify and analyze micro- and nanoscale particles contained in a sample solution according to the specific embodiments as described herein.

In certain embodiments, provided herein are devices and methods configured to quantify, isolate and further analyze particles sized at the micro- to nanoscale within a fluid solution. In particular embodiments, the present invention provides multi-planar, microelectrode array devices capable of using electrokinetics to influence and control particle motion in fluids for quantification and recovery of such particles. The microelectrode array device of the present invention, through the configuration and arrangement of electrodes within the device, recovers particles based on parameters such as effective stokes radius (size) permittivity and inherent dielectric properties specific to the particles rather than properties of the surrounding fluid. In other aspects, the multi-planar, microelectrode array devices are comprised of non-standard fabrication techniques resulting in unique electrode arrangements, the geometries of which allow for enhanced performance of the devices relative to particle isolation. In another aspect, the multi-planar, microelectrode array devices of the present invention overcome frequency and amplitude limitations present in the devices of the prior art as the conductivity or salinity increases to that of physiological or biological fluids. Similarly, the devices of the present invention eliminates limitations associated with the mixing of sample solutions as conductivity or salinity decreases to that of de-ionized water.

In some embodiments, the devices of the present invention contain a dielectric or semiconductor substrate upon which electrodes are arranged using certain techniques, including but not limited to, photolithography, vapor deposition, sputtering, screen printing, 3D printing or electroplating. The composition of the substrate is at least one of glass, silicon or a nonconductive polymer selected from the group consisting of acrylic, polyethylene terephthalate and cyclic olefin copolymer.

As described in FIG. 1A, a preferred embodiment consists of a solid type fabrication model wherein the microelectrode array devices of the present invention are generated using custom or non-standard fabrication techniques. Such techniques enable unique electrode geometries to be created which allow for new and enhanced performance features not considered possible in the prior art.

Figure 1B:
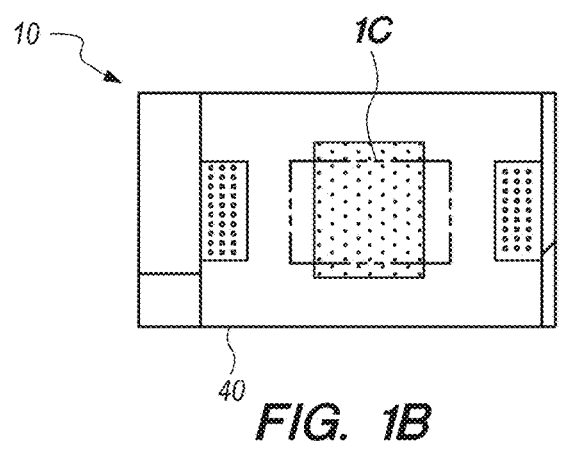
Figure 1C:
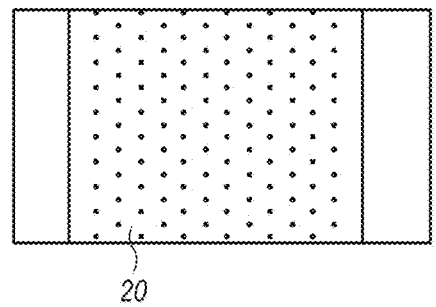

The devices of the present invention are preferably arranged in layers, wherein each layer may be arranged according to a custom fabrication determined in advance. In a preferred embodiment, as described in FIG. 1B, a housing 10 comprises at least one cartridge 40 containing a plurality of electrodes 20 arranged in a geometric pattern may be embedded within the housing 10 to accommodate a fluid passing through the cartridge 40 by way of channels 50. As evidenced in FIG. 1, it is a preferred embodiment to have a series of cartridges, each cartridge 40 containing a plurality of electrodes 20 comprising a unique geometric pattern, embedded within a housing 10 to accommodate a fluid passing over the plurality of electrodes 20 by way of channels 50.

Figure 2:
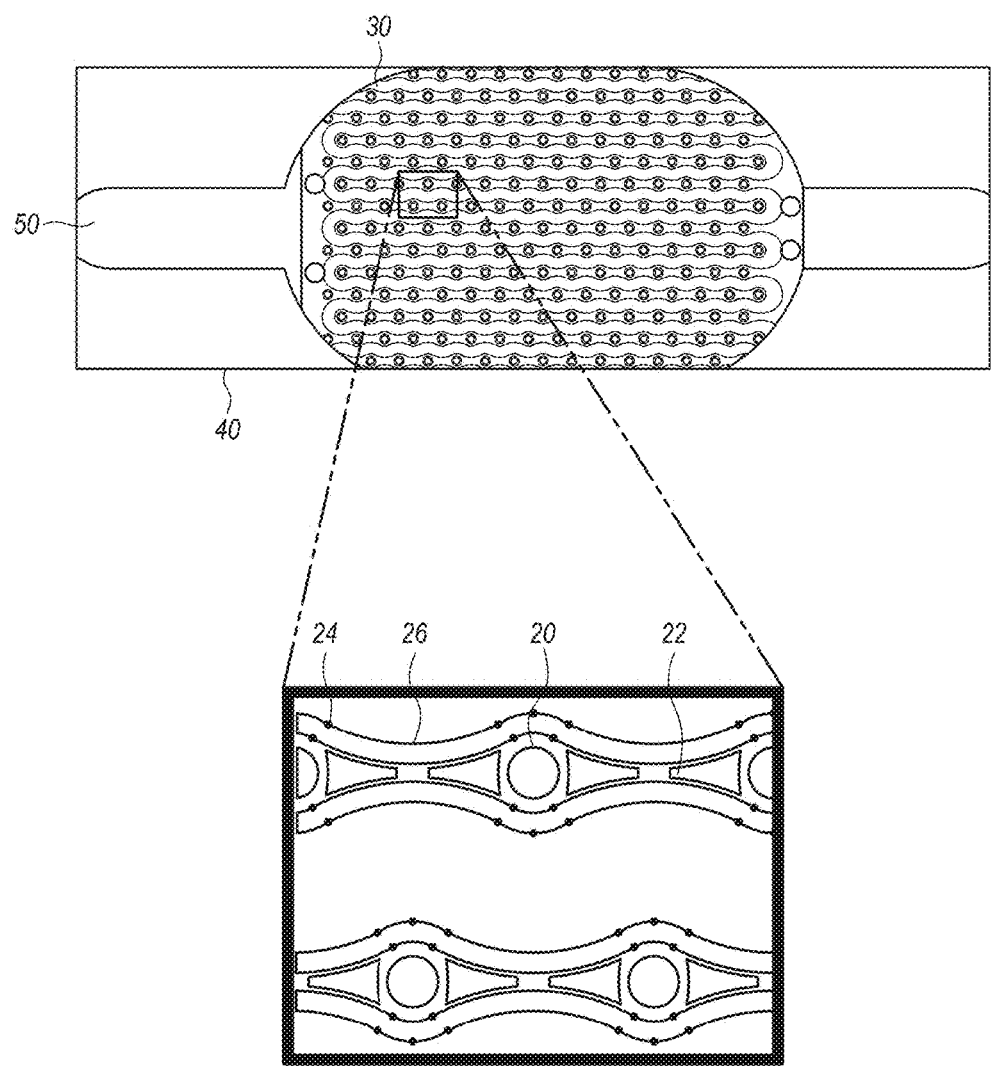
FIG. 2 shows a detailed schematic of the microelectrode array according to one embodiment of varying at least three electrodes having three independent, separate charges. Detailed view depicts location of impedance sensors around insulated electrodes, bordered by impedance bridges.

In preferred embodiments, as shown in FIG. 2, a plurality of electrodes 20 are deposited or arranged at particular locations on or within a substrate 30 embedded with a cartridge 40 having channels 50. In one aspect, the plurality of electrodes 20 are made of a metal or, optionally, a non-metallic, conductive material. In another aspect, the electrode material comprises at least one metal selected from the group consisting of gold, platinum, palladium, iridium, carbon, platinized carbon and indium tin oxide. In a preferred aspect, each electrode 20 has a thickness range of from about 10 nm to about 1000 nm. Electrode arrangements are configured to provide both insulated and non-insulated fields. Preferably, the insulated and non-insulated electrodes are activated independently of each other and can be simultaneously active. Optionally, the insulated and non-insulated electrodes are delayed in phase by up to about 90 degrees.

The magnified view of FIG. 2 depicts a close-up view of the preferred arrangement of the electrodes 20. Specifically, each electrode 20 within this view of three may accommodate a different charge (or the same charge) relative to its neighbor. The three electrodes 20 are positioned within a substrate 30. Impedance bridges 22 are positioned on either side of each electrode 20. A series of impedance sensors 24 are arranged within the border of insulated traces 26 that may run horizontal or diagonal across the electrodes 20.

In yet another embodiment, the electrode arrangement allows for the decoupling of the DEP forces from the ETF and EOF forces. In one aspect, this decoupling is achieved through the spatial removal of the high field and low field DEP regions from the high strength and low strength regions of the ETF and EOF forces. Preferably, the electrode arrangement provides a translocation of the high field DEP region to a position proximal to the beginning of the downward flow dead zone in order to isolate a particle contained in the fluid. The range of this preferred area is within about 0 nm to about 10000 nm. In yet another aspect, the electrodes can be continuous, circular or elliptical in physical form, with an angle of orientation between adjacent electrodes being 0, 30 60, or 90 degrees.

In another preferred embodiment, the multi-planar, microelectrode array devices of the present invention are coupled to a power source, wherein the devices can handle up to about 3 A or 3000 mA. Preferably, each individual electrodes are powered up to about 0.1 A or 100 mA, or just before signal integrity is compromised due to electrolysis and degradation at the electrode.

Figure 3:
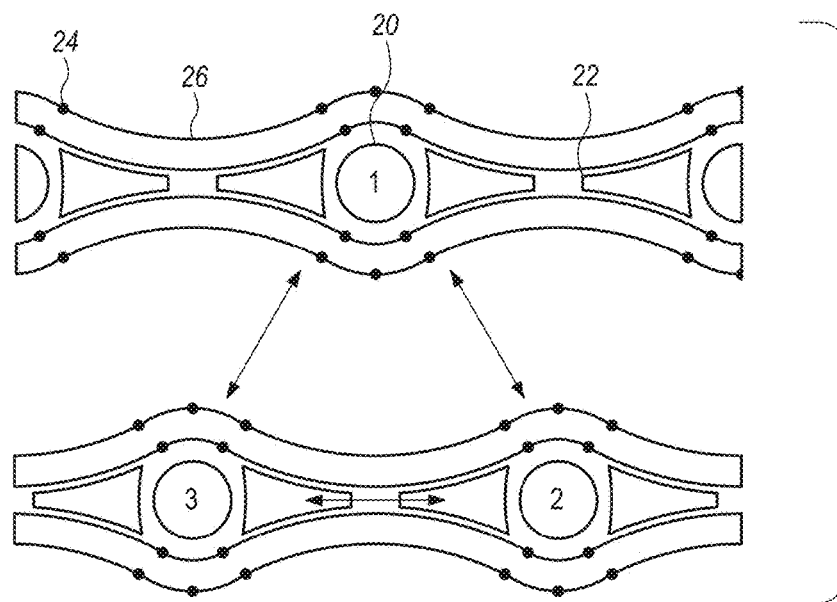
FIG. 3 shows an example of the interrelated charges across three microelectrodes in proximity to each other in one embodiment of the microelectrode array devices of the present invention.

As further described in FIG. 3, the three electrodes 20 (from the magnified view of FIG. 2) will preferably have at least three separate polarities, wherein the charge on each electrode 20 may be modified independent of the other proximately positioned electrodes 20, with each charge being either positive (+), negative (−) or neutral. Preferably, the electrodes 20 enable a non-uniform electric field (black arrows) based on the time dependent polarity of each electrode relative to each electrode. The electrode arrangement can be configured such that the charge of each electrode 20 may be modified independent of any other electrode 20, with each charge being capable of exhibiting a positive, negative or neutral charge at any given time. Examples of preferred arrangement of polarity within a given set of three electrodes 20 can be as follows, from the top most electrode moving clockwise: (+), (−), neutral; (+), neutral, (−); (−), (+), neutral; (−), neutral, (+); neutral, (+), (−); neutral, (−), (+); (+), (+), (−); (+), (−), (+); (−), (−), (+); and (−), (+), (−).

In a most preferred embodiment, there are at least two different planes in the Z-dimension between independent, adjacent electrodes, thereby modifying the non-uniformity of the electric field. By having at least two different planes in the Z-dimension between each adjacent electrode, there further provides an offset to remove the uniform gradient of the electric field about each electrode, which then alters the flow dynamics of the ETF and EOF forces. Similarly, providing at least two different planes about the Z-dimension between each adjacent electrode results in changes in the DEP high field and low field forces. The distance of the Z-dimension between adjacent electrodes can be between about 10 nm to about 1000 nm. Preferably, the electrodes in the electrode arrangement have independent yaw, pitch and roll with respect to each other. Most preferably, the yaw can vary from about 0 degrees to about 179.9 degrees between adjacent electrodes and the pitch and roll can vary from about 0 degrees to about 89.9 degrees from the substrate plane. In a preferred embodiment, the three independent, adjacent electrodes would all have a pitch at an angle of 89.9 degrees with respect to the substrate plane, with a yaw angled such that the peaks of the independent, adjacent electrodes (as determined by the pitch) would be facing inward towards each other. The preferred embodiment for the roll angle would be arranged such that the peaks of the independent, adjacent electrodes (determined by the pitch) are at an angle of about 45 degrees with respect to the substrate plane.

Figure 4:
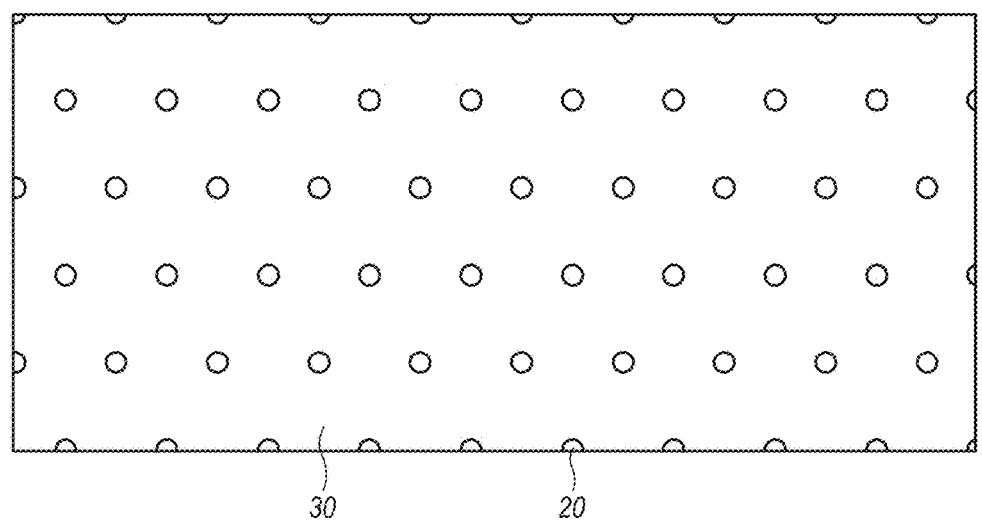
FIG. 4 shows a top view of one embodiment of the microelectrode array, depicting exposed electrodes embedded within a dielectric material layer.

As shown in FIG. 4, the plurality of electrodes 20 is present in a preferred geometric array, wherein the electrodes 20 are embedded with a substrate 30 comprising of a dielectric material. In this top view of the first layer, only the exposed electrodes 20 are shown surrounding by the dielectric substrate 30.

Figure 5:
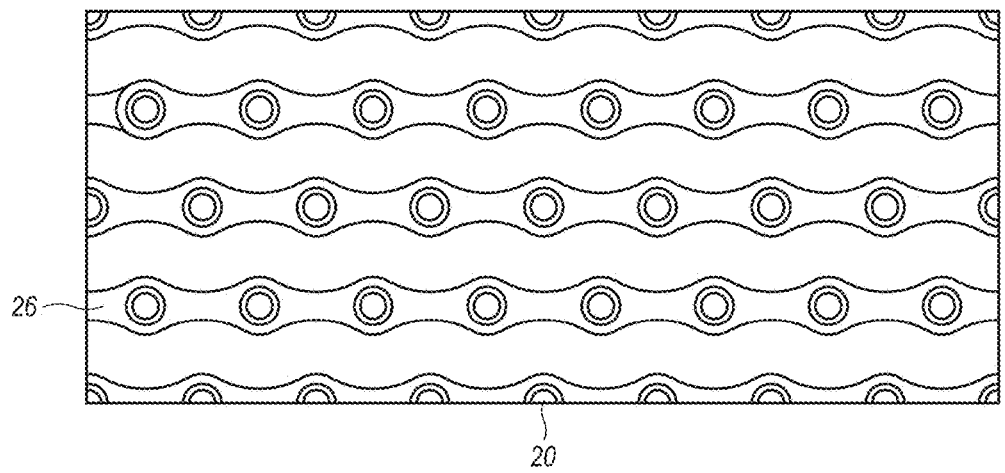
FIG. 5 shows a top view of the embodiment of the microelectrode array from FIG. 4 except the dielectric material layer is removed, revealing an example configuration of trace patterns for additional electrodes insulated from the fluid sample.

FIG. 5 shows the top view of the microelectrode array from FIG. 4, but with the dielectric material removed, revealing an example configuration of insulated traces 26 arranged horizontal to the rows of electrodes 20. Exposed electrodes 20 are present surrounding by the insulated traces 26.

In some embodiments, the devices of the present invention provide for multi-planar floating electrodes in the Z-dimension within a dielectric substrate, wherein the floating electrodes are not connected to any power source. This results in a cascading production of the electric field as it passes through the floating electrodes. Preferably, the distance between the floating electrodes in the Z dimension varies from about 10 nm to about 100 nm.

Figure 6:
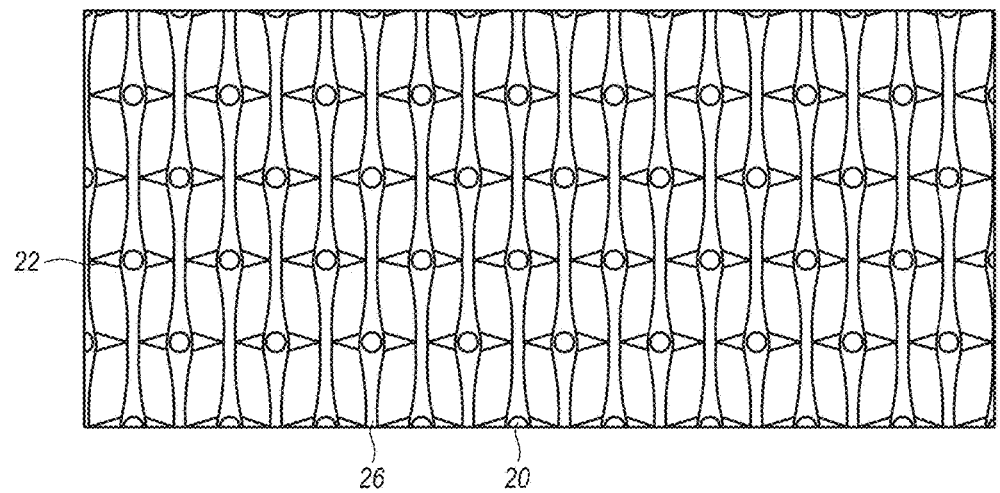
FIG. 6 show a top view of the embodiment of the microelectrode array from FIG. 5 with the configuration of the trace patterns for the independent electrodes coupled with the impedance bridge (magenta) embedded within the microelectrode array substrate.

In some aspects, the devices and methods of the present invention further provide for at least one impedance bridge circuit between electrodes to modulate capacitance with the substrate. As shown in FIG. 6, a top view of an alternative embodiment depicts a vertical row of insulated traces 26 with the presence of impedance bridges 22 on either side of each individual electrode 20 within the array. The presence of the impedance bridge circuit eliminates the capacitance coupling throughout the substrate and further provides a heat source through the substrate.

Figure 7A:
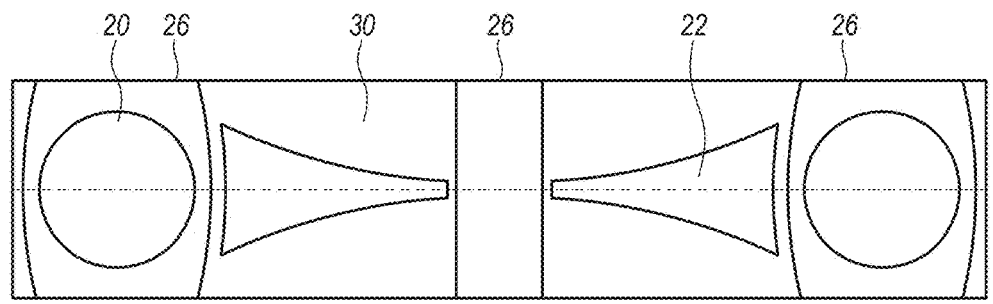
FIGS. 7A-7C show the impedance bridge element of the microelectrode array devices of the present invention. (A) shows a magnified, top view of the impedance bridge in between two electrodes; (B) depicts a cross sectional view of (A) detailing the liquid-filled microfluidic chamber and the direction of the current flowing through the liquid; (C) shows an AC equivalent circuit model of the fluidic path within the device.
Figure 7B:
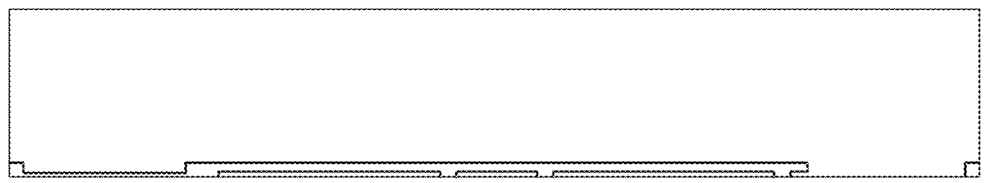
Figure 7C:
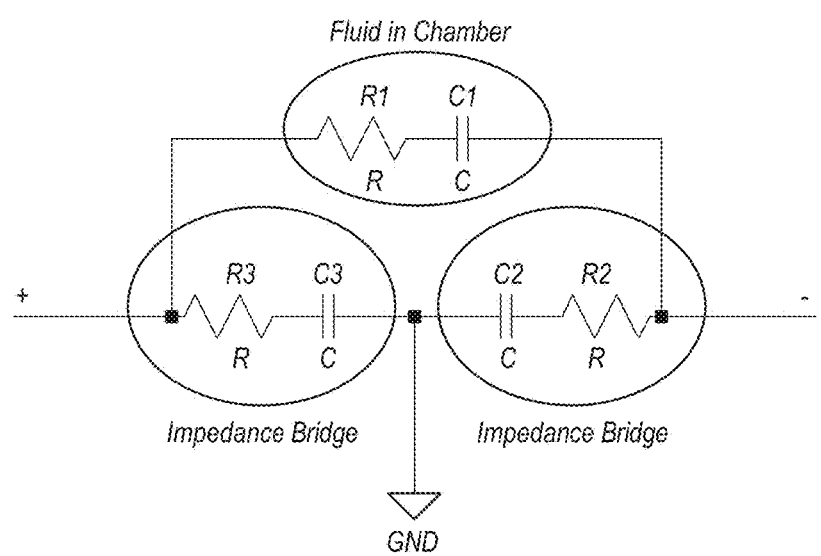

As evidenced in FIG. 7A, a magnified view of an impedance bridge 22 is shown between a pair of electrodes 20. Insulated traces 26 run in a vertical direction around each electrode 20 within the dielectric material 30. In between each impedance bridge 22 exists an insulated trace 26. A cross-sectional view (FIG. 7B) shows the presence of fluid above the microelectrode array and the relative distances between each electrode 20, as well as their height above the base. FIG. 7C shows alternating current equivalent circuit model of the fluidic path within the device.

In certain embodiments, methods of fabricating devices of the present invention comprise providing cavities built into the substrate, such cavities taking the shapes of pits, valleys or channels in order to generate certain temperature gradients throughout the device. In one aspect, the methods of fabricating devices of the present invention further comprise a dielectric passivation layer covering deposited electrode material. Preferably, the dielectric passivation layer selectively exposes certain regions of the substrate. In another aspect, the passivation materials can be comprised of at least one substance selected from the group consisting of silicon dioxide, silicon nitride, aluminum oxide and any other substrate having a dielectric constant (k-value) of less than 4.0. The thickness of the passivation layer can range from about 0.1 µm to about 20 µm.

In some embodiments, the methods and devices of the present invention include a field effect transistor, allowing for quantification of particles influenced by the electric field and electrode performance within the device. Preferably, the devices of the present invention are fabricated to include at least one or more field effect transistors per each exposed electrode. This will enable the measurement of any degradation at the surface of each electrode. The field effect transistor will also track and measure pH changes at the surface of each electrode in the arrangement.

In further embodiments, the methods and devices of the present invention further provide for impedance sensors to be integrated within the substrate of the device. The presence of the impedance sensors enables quantification of particles influenced by the electric field. Additionally, the impedance sensors are capable of tracking and measuring electrode performance. Preferably, there is at least one or more impedance sensors per exposed electrode in the arrangement within the device. Most preferably, the impedance sensors can track electrode pH and surface degradation of each electrode.

Figure 8A:
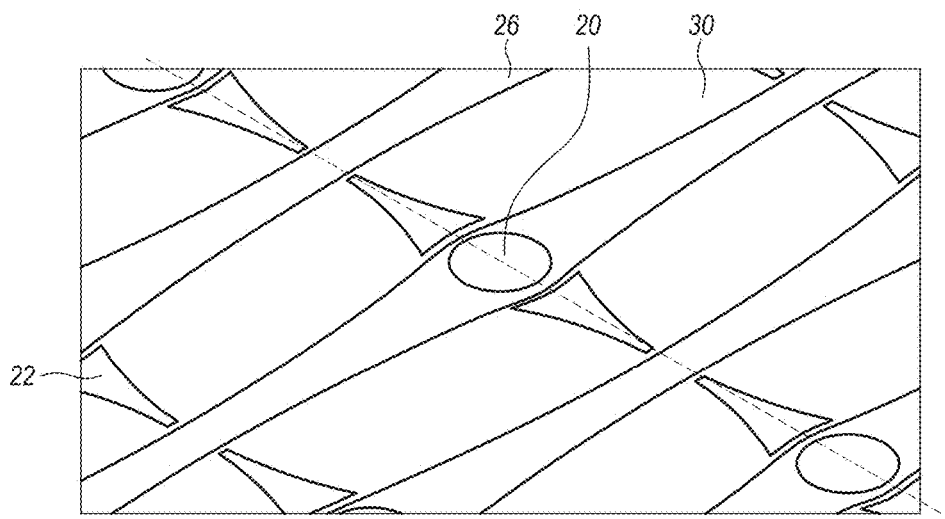
FIGS. 8A-8B show one embodiment of different Z-heights of electrodes within the array. (A) depicts a perspective view of the impedance bridge arrangement across the electrodes, wherein the central electrode has a different height in the Z-dimension; (B) shows a cross-sectional view along with an example of the different Z-dimension heights of one of the electrodes.
Figure 8B:
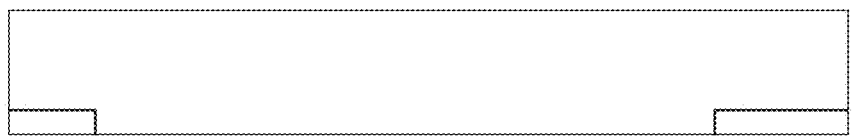

As shown in FIG. 8A, a perspective view of the microelectrode array displays a different in height in the Z-dimension between not only adjacent electrodes, but even with respect to opposing sides of the same electrode 20. A cross-sectional view (FIG. 8B) further shows the difference in Z-height between opposing sides of each electrode 20.

The devices of the present invention do not require the presence of a swellable, porous passivation layer over the exposed electrodes that is a feature of devices within the prior art. Preferably, the devices of the present invention comprise for a fluidic chamber that holds a sample solution directly over the microelectrode array. The fluidic channels provide for channeling the sample solution directly over the electrode arrangement. Most preferably, the fluidic channels can expand or collapse based on either an electronic or temperature stimulus.

In certain embodiments, the fabrication methods to create the devices of the present invention comprise use of 3D printing, screen printing, laser sintering, laser ablation or photolithography techniques in creating non-flat, planar structures within each device. Utilization of at least one of the above identified techniques allow for unique electrode geometries to be applied within the substrate of the devices of the present invention. Preferably, these manufacturing processes allow for the influencing, isolating, quantifying and recovering of particles in a variety of fluid compositions, with consistent device performance in fluid conductivity measurements of up to 50 mS/cm.

In preferred embodiments, the devices of the present invention can generate non-uniform electric fields when sourced with a power supply that delivers a signal selected from the group consisting of an alternating current, direct current and pulsed direct current. The signals delivered to the devices of the present invention can be any arbitrary waveform, including sine, square, triangle, continuous or any combination of the above, further comprising a modified duty cycle with accompanying frequency.

In other aspects, devices of the present invention are capable of function in fluids or sample solutions with conductivity ranging from about 0 S/m to about 5 S/m, from about 0 S/cm to about 0.05 S/cm and from about 0 mS/cm to about 50 mS/cm. Optionally, the fluids may be from natural or physiological sources. The fluids may also comprise synthetic or adulterated components in order to reduce the conductivity of the fluids. The fluids may be sourced from one selected from the group consisting of de-ionized water, physiological, biological and brackish water. In another aspect, the fluid viscosity within a sample solution can range from about 1 cP to about 100 cP or from about 0.0001 Pascal second to about 0.1 Pascal second.

In another aspect, the devices of the present invention can comprised specific geometric arrays of microelectrodes comprising an ability to influence particles ranging, in diameter, from about 10 nm to about 50,000 nm. The particles to be identified by the devices of the present invention can include cellular and subcellular particles, as well as synthetic or non-biological particles, including dextran, polystyrene micro-spheres, polystyrene nano-spheres and other natural or synthetic polymers.

In yet another aspect, the microelectrode array devices of the present invention comprise generation of a DEP high field and low field region across a fluid or sample solution, wherein the high field region and low field region are determined based on electric field strength and specific geometry of insulated and non-insulated electrodes. The geometry of the electrodes allow for the devices of the present invention to generate ETF and EOF forces within the fluid flow, with flow rates ranging from about 0.01 µL/min to about 1 mL/min. In a most preferred embodiment, the devices of the present invention can separate particles based on their effective stokes radius and dielectric properties specific to each particle inside the microfluidic environment. In another preferred aspect, the separation of the particles is based on the applied frequency and amplitude of the signal from the power source, the signal selected from the group consisting of alternating current, direct current and pulsed direct current. The amplitude range for insulated electrodes comprise from about 1 Volts Peak-to-Peak (Vpp) to about 3000 Vpp. The amplitude range for non-insulated electrodes comprises from about 1 to about 30 Vpp. The frequency range delivered to the microelectrode array can range from about 1 Hz to about 1 MHz.

In one aspect, the methods and devices of the present invention comprise quantification of particles in a solution comprising measuring a change in current or impedance using a field effect transistor. Optionally, this quantification can occur in real-time, such as when particles influenced by an electric field enter the DEP depletion zone. Alternatively, this quantification can occur during a specific event, such when the particles are immobilized in a DEP high field region or low field region. Similarly, the quantification can occur after a specific event, such as when particles are released in a DEP high field region or low field region.

In another aspect, the methods and devices of the present invention comprise quantification of particles in a solution comprising measuring a change in impedance using electrical impedance tomography or impedance spectroscopy. Optionally, this quantification can occur in real-time, such as when particles influenced by an electric field enter the DEP depletion zone. Alternatively, this quantification can occur during a specific event, such when the particles are immobilized in a DEP high field region or low field region. Similarly, the quantification can occur after a specific event, such as when particles are released in a DEP high field region or low field region.

In yet another aspect, the methods and devices of the present invention comprise quantification of particles in a solution comprising measuring a change in fluorescence using optical microscopy. Optionally, this quantification can occur in real-time, such as when particles influenced by an electric field enter the DEP depletion zone. Alternatively, this quantification can occur during a specific event, such as when the particles are immobilized in a DEP high field region or low field region. Similarly, the quantification can occur after a specific event, such as when particles are released in a DEP high field region or low field region. Preferably, the optical microscopy measurement are made using an opto-acoustic monochromator or filters in order to select specific wavelengths of light. Optionally, a photo multiplier tube, avalanche photo diode or at least one of a member selected from the group consisting of wide-field, confocal and super resolution fluorescence microscopy coupled with a charge coupled device or complementary metal oxide semiconductor detector is used to further quantify any isolated particles. In a most preferred embodiment, optical measurements are made using wavelengths ranging from about 360 nm to about 900 nm.

In certain embodiments, the devices of the present invention comprise a power source delivering at least one input signal to the electrode arrangement within the substrate of each device, the at least one input signal comprising a waveform selected from the group consisting of a sine, square and triangle. Preferably, electric input signals for insulated electrodes can be the same or different than those signals for non-insulated electrodes with respect to frequency, phase and amplitude. Further, the electric input signals can be a combination of different frequencies applied simultaneously, and independently across each electrode. Optionally, the electric input signals can alternate between low and high frequencies. In a preferred embodiment, the electrode arrangements receiving the electric input signals can be all be independently set to either positive, negative or neutral during signal delivery. In an alternative embodiment, the polarity of the signal varies at each electrode in either random or programmable patterns. This enables modification of bulk fluid flow throughout the fluidic chamber, thereby creating an additional or supplemental form of fluidic mixing which is capable of replenishing the particle depletion zone and enhancing overall capture efficiency of particles within the device.

EXAMPLES

Figure 9A:
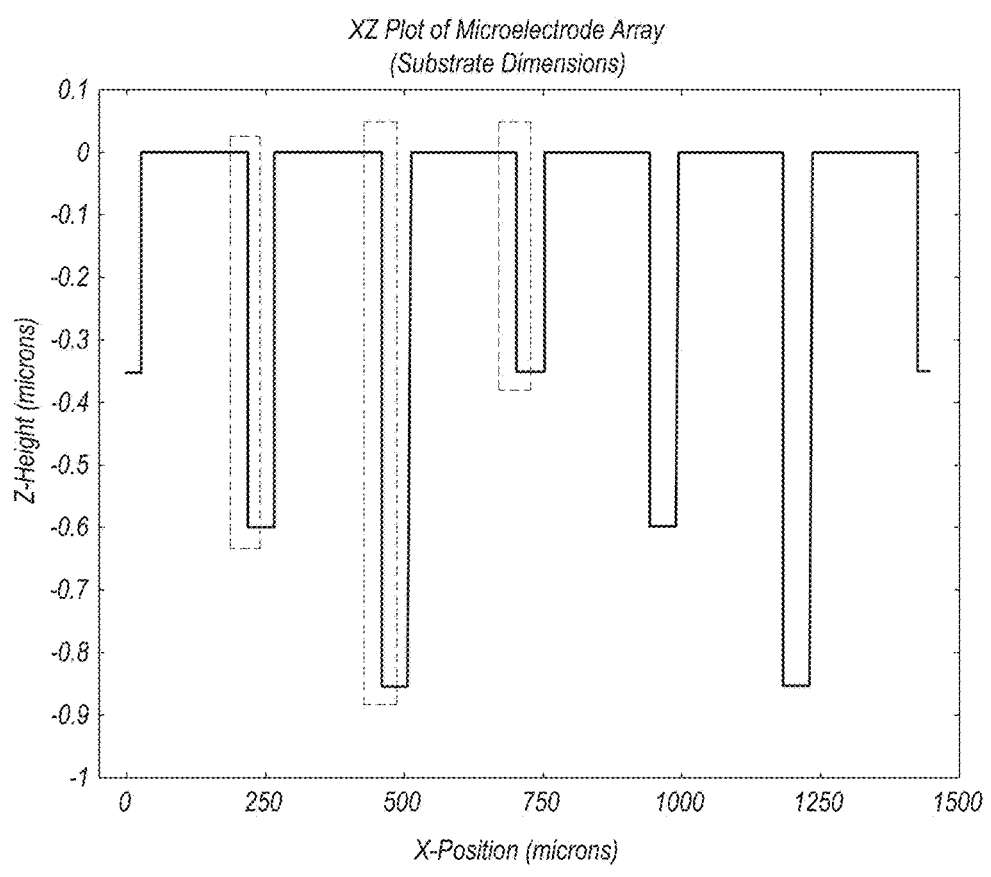
FIGS. 9A-9D show the relationship between Z-height and electric field gradients ($\nabla E^2$) between electrodes. (A) shows an X- and Z-dimension plot of the electric field based on neighboring electrodes; (B) is a plot of the electric field gradient ($\nabla E^2$) for medium Z-height; (C) long Z-height; (D) shortest Z-height. (B)-(D) reference the dashed line at each electrode from (A), moving left to right.
Figure 9B:
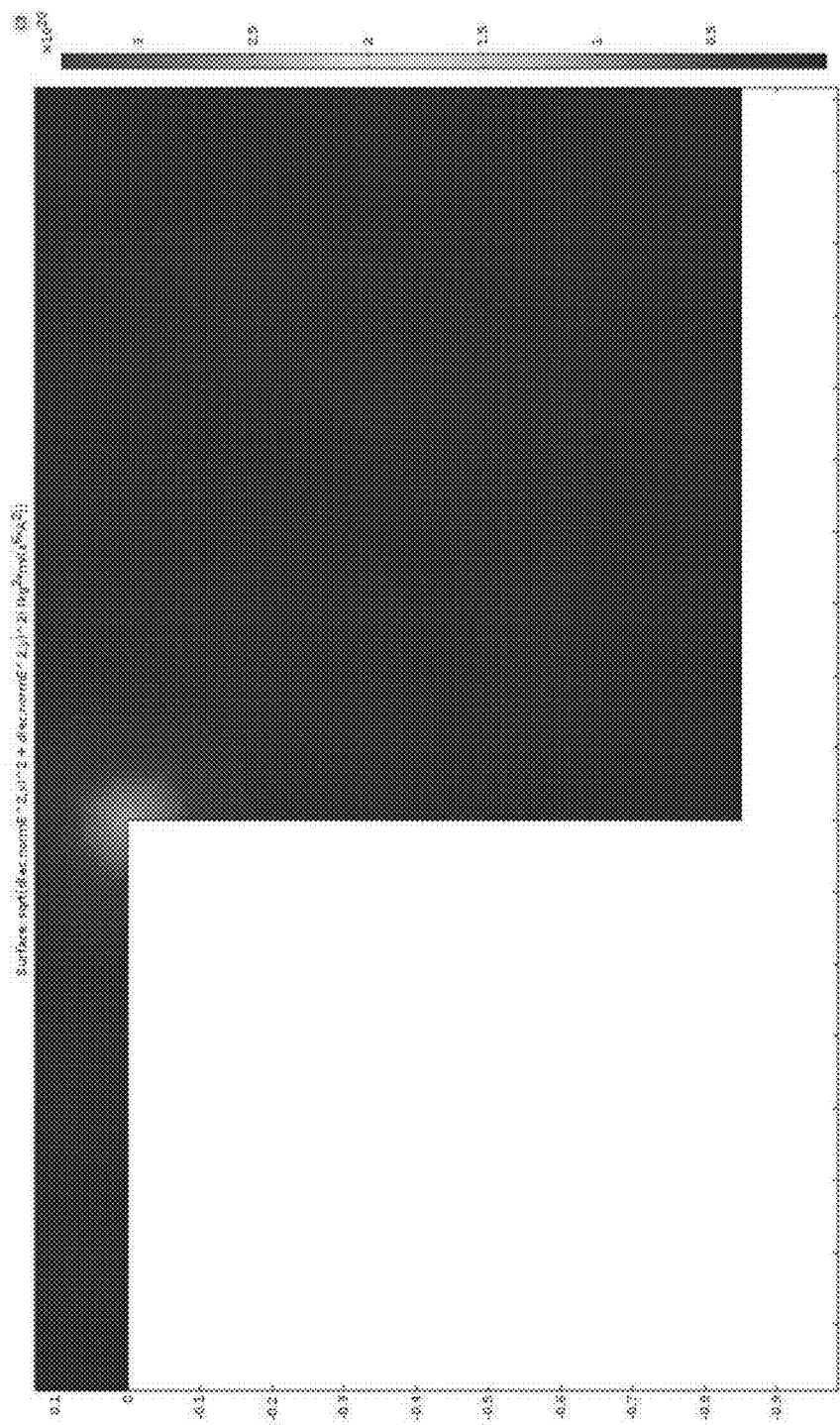
Figure 9C:
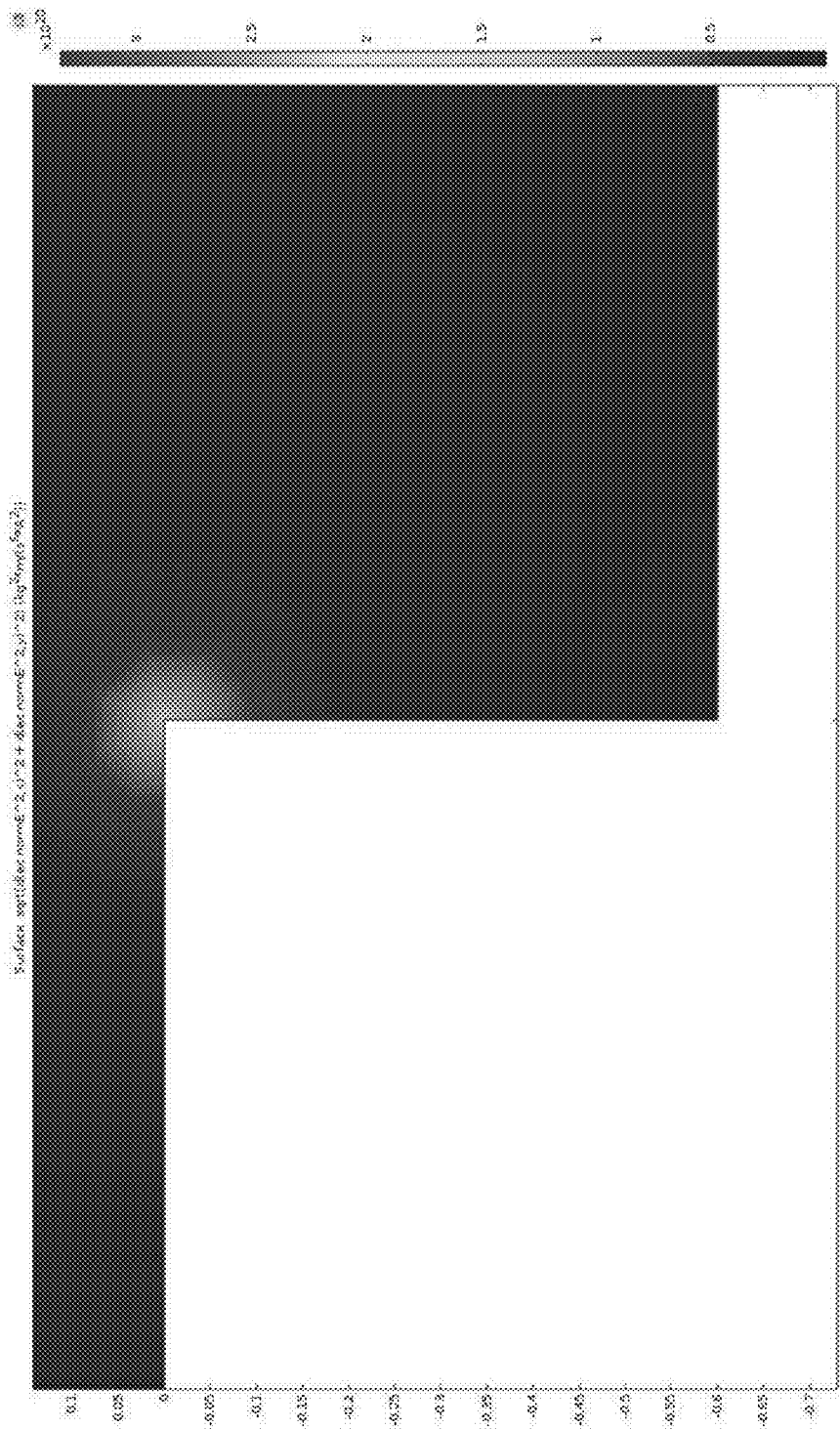

I. Representative Gradients and Changes to the Electric Field Based on Differing Z-Height of Individual Electrodes As shown in FIG. 9A-9D, experimental evidence was gathered by mapping changes in the gradient of the electric field, as expressed by $\nabla E^2$, with respect to different electrode heights in the Z-dimension. FIG. 9A is a plot of the microelectrode array showing substrate dimensions, with electrode positions across the X-dimension (in microns) relative to the height of the electrode in the Z-dimension (Z-height in microns).

Figure 9D:
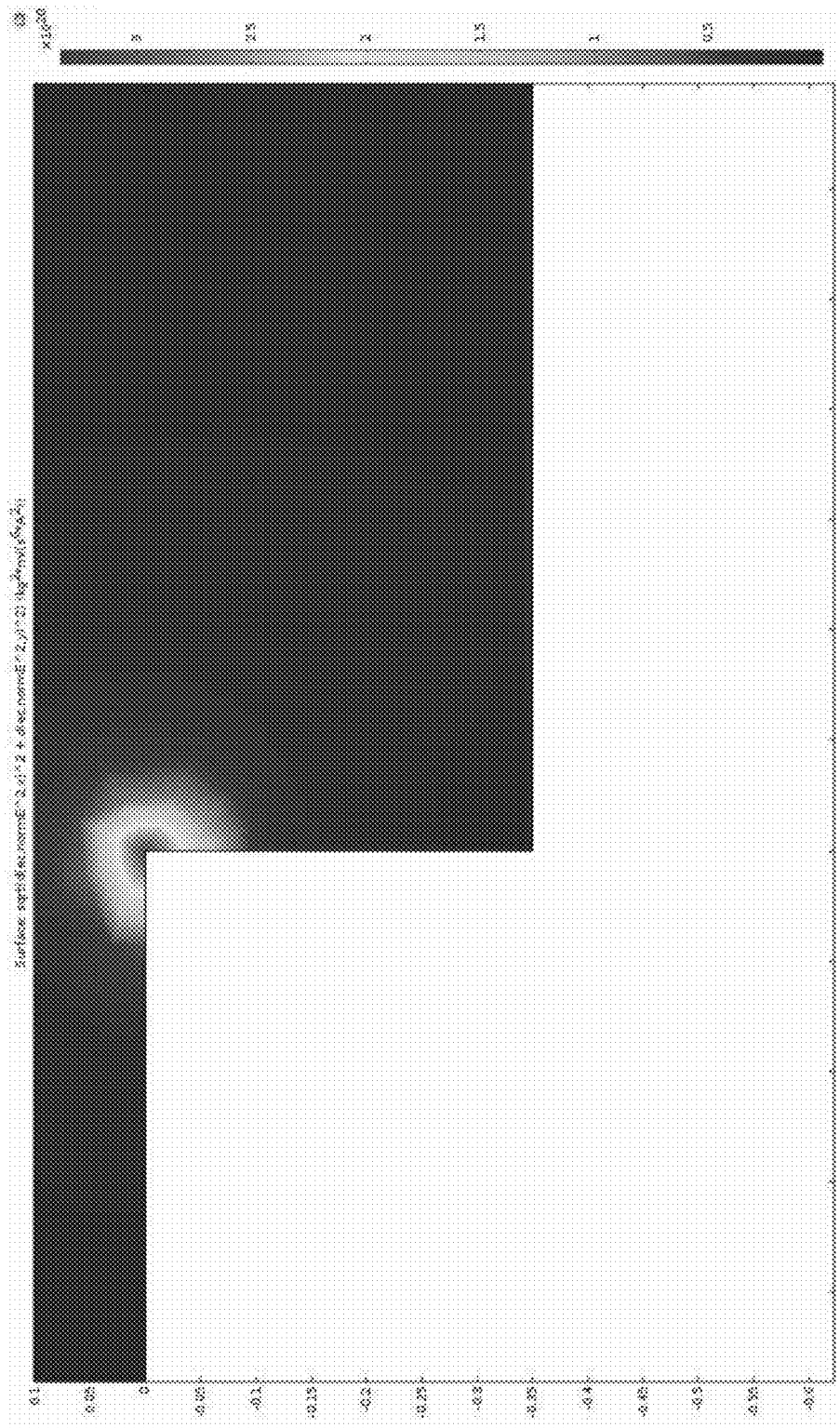

Measuring the gradient of the changes in the electric field vary based on the changing of the height of the electrode in the Z-dimension. Moving left to right across the XZ plot of FIG. 9A, observations were taken from an electrode having medium height (FIG. 9B), a longest height (FIG. 9C) and the shortest relative height (FIG. 9D). It is clear that the magnitude of change across the electric field gradient is correlated with the height of the electrode in the Z-dimension, such that the strongest intensity comes from a shorter electrode height relative to a longer height.

II. Experiment Showing Electric Field Gradient Changes for Different Electrode Options Compared to Uniform Electrode Height The devices of the prior art all have a uniform height of each electrode in the array in order to standardize experimental protocols. The devices of the present invention, on the other hand, have the ability to alter each individual electrode in the Z-height in order to take advantage of increased particle capture rates through the separation of DEP forces from the forces that derive ET and EO flow.

Figure 10A:
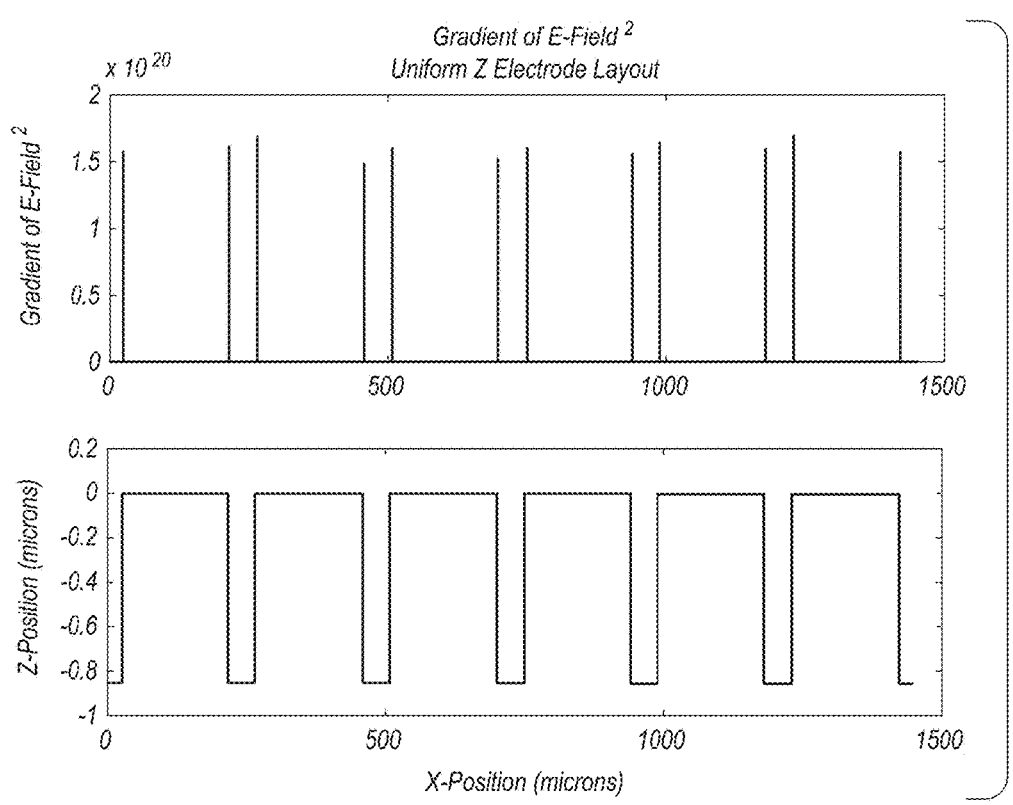
FIGS. 10A-10C show evidence of electric field gradient patterns when comparing the devices of the present invention with those found in the prior art. (A) is a line graph showing the electric field within an array comprised of electrodes having uniform Z-height, along with the respective XZ plot of the electrode pattern; (B) line graph depicting non-uniform Z-height of electrodes and the attendant changes in the electric field gradient, along with the respective XZ plot of the non-uniform Z-height electrode pattern; (C) line graph depicting non-uniform Z-height electrodes coupled with roll at two electrodes and the attendant changes in the electric field gradient, along with the respective XZ plot of the non-uniform Z-height electrodes with roll.
Figure 10B:
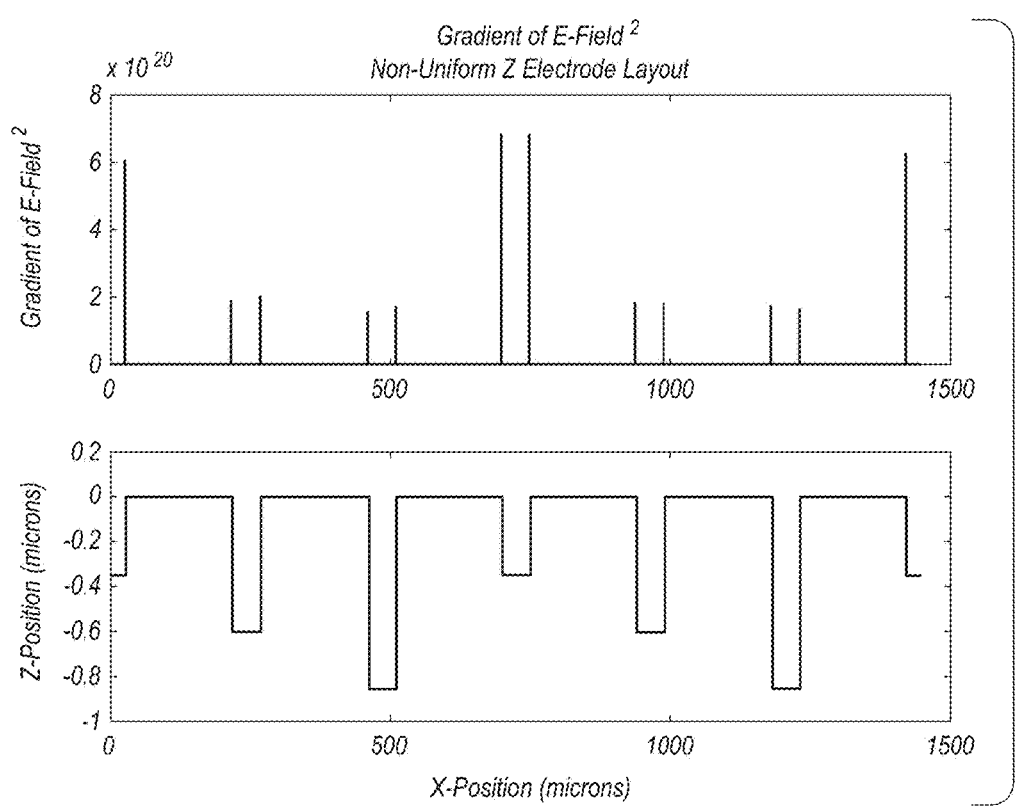
Figure 10C:
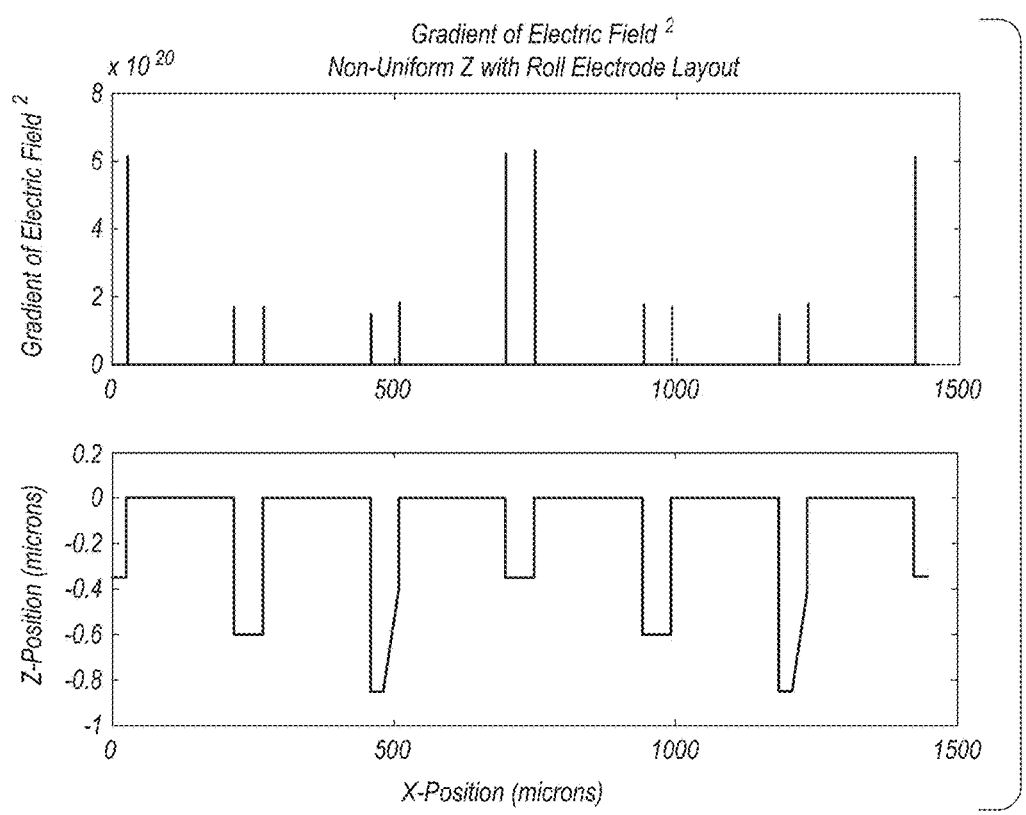

As shown in FIG. 10A, a line graph is presented showing the constant electric field gradient across electrodes have a uniform Z-height across the array. In contrast, FIG. 10B shows line graph data depicting non-uniform Z-height of electrodes and the attendant changes in the electric field gradient based on the differing electrode height. FIG. 10C goes even farther when incorporating the roll aspect to two electrodes and the respective changes in the electric field based on same. As can be shown in these line graphs, the electric field is capable of being severely altered based on the preferred embodiments within the present invention, resulting in more efficient capture rates for particles contained in a fluid.

III. Experimental Protocols for Device Utilization

A. Protocol Specific for Capture, Release and Elute of Particles Contained in Fluid Solution:

(1) Load fluid specimen into microfluidic chamber and apply an E-Field of 30 Vpp to the non-insulated electrodes at a frequency of 50 kHz;

(2) apply an E-Field of 1500 Vpp to the insulated electrodes at a frequency of 1000 Hz;

(3) enable capture for 10 minutes;

(4) after the 10 minutes, apply a pressure driven flow of 10 µL/min and wash away original fluid specimen with desired recovery buffer;

(5) after original fluid specimen is removed, turn off E-Field applied to insulated and non-insulated electrodes and release immobilized particles into recovery buffer; and (6) remove recovery buffer from microfluidic chamber for secondary analysis.

B. Protocol Specific for Capture and Quantification of Particles Contained in Fluid Solution:

(1) Load fluid specimen into microfluidic chamber and apply an E-Field of 30 Vpp to the non-insulated electrodes at a frequency of 50 kHz;

(2) apply an E-Field of 1500 Vpp to the insulated electrodes at a frequency of 1000 Hz;

(3) enable capture for 10 minutes;

(4) during 10 minutes of capture, monitor the change in impedance on impedance sensors to determine rate of particle immobilization or rate of DEP influence on particles found in the fluid.

IV. Preferred Positions with Respect to Yaw, Pitch and Roll of Three Adjacent, Independent Electrodes within an Array The microelectrode array within the devices of the present invention include a plurality of electrodes, with each electrode being capable of independent manipulation of a variety of parameters, including altering certain angles of yaw, pitch and roll with respect to the substrate plane. The interrelationship between this multi-planar motion and each neighboring electrode's position is fundamental to the processing of samples through optimal stirring/mixing in order to isolate the particles within each fluid sample.

Figure 11:
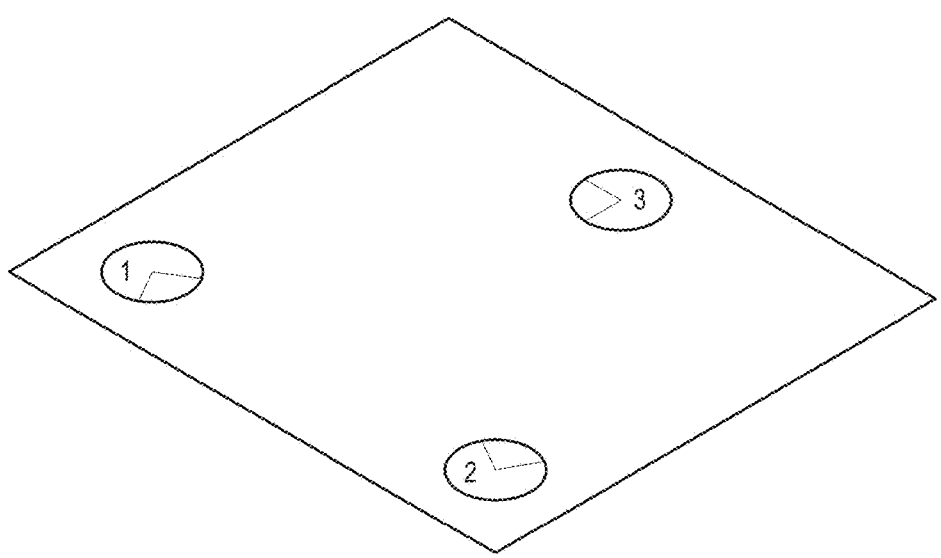
FIG. 11 shows a preferred arrangement between a set of three adjacent, independent electrodes within a microelectrode array of a device of the present invention.

FIG. 11 shows the optimal orientation across a series of three adjacent, independent electrodes with respect to one another. Electrode 1 (E1) is positioned to face electrode 2 (E2) which is angled to face electrode 3 (E3), which in turn is positioned to face E1. This arrangement of E1 to E2 to E3 and back to E1 creates optimal stirring about the center of the three electrodes in the Z-dimension.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. A microfluidics device comprising:
   (a) a housing in the form of at least one cartridge;
   (b) a microelectrode array, comprising:
      (i) an electrode arrangement of a plurality of electrodes, wherein the electrode arrangement is configured using three or more separate input signals to independently operate at least three different polarity configurations at any given time;
      (ii) a dielectric substrate, wherein the dielectric substrate further comprises the electrode arrangement arranged in a geometric pattern and is deposited within the at least one cartridge;
      (iii) an impedance bridge circuit between adjacent electrodes of the electrode arrangement, wherein the impedance bridge comprises insulated and isolated conductive material surrounded by dielectric material;
      (iv) at least two different planes in a Z dimension between electrodes of the electrode arrangement, wherein the Z dimension varies from 10 nm to 1000 nm; and
      (v) individual electrodes within the plurality of electrodes that have independent yaw, pitch and roll with respect to each other, and
   (c) at least one channel, wherein a fluid may be passed through at least one inlet port and exited through at least one outlet port.

2. The device of claim 1, wherein the at least one channel is arranged to accommodate the fluid so that it passes over the microelectrode array.

3. The device of claim 1, wherein the plurality of electrodes are deposited within the dielectric substrate using a means selected from the group consisting of photolithography, vapor deposition, sputtering, screen printing, three dimensional (3D) printing and electroplating.

4. The device of claim 1, wherein the dielectric substrate is composed of at least one of glass, silicon and a nonconductive polymer.

5. The device of claim 1, wherein the plurality of electrodes are each made of metal or a non-metallic conductive material.

6. The device of claim 1, wherein the plurality of electrodes have a thickness from about 10 nm to about 10 μm.

7. The device of claim 1, wherein the electrodes within the electrode arrangement are configured to provide insulated and non-insulated electric fields.

8. The device of claim 1, wherein the plurality of electrodes are geometrically configured to facilitate the decoupling of the dielectrophoretic forces from the forces derived from electrothermal and electroosmotic flow.

9. The device of claim 1, wherein the plurality of electrodes are each substantially circular in shape with an angle of orientation between adjacent electrodes from about 0 degrees to about 90 degrees.

10. The device of claim 1, wherein each individual electrode within the plurality of electrodes can carry a charge that is positive (+), negative (−) or neutral.

11. The device of claim 10, wherein the each individual electrode may vary the charge relative to the most proximate electrode in the microelectrode array.

12. The device of claim 1, further comprising at least one field effect transistor.

13. A method of processing fluid in order to analyze and extract particles within the fluid comprising:
   (a) providing the microfluidics device of claim 1;
   (b) exposing the plurality of electrodes to a fluid;
   (c) providing a non-uniform electric field throughout the fluid;
   (d) measuring a change in current or impedance using a field effect transistor at a particular time point; and
   (e) quantifying the particles in the fluid once the particles have entered a dielectrophoretic depletion zone.

14. A method of quantifying at least one particle in a fluid solution comprising;
   (a) providing the microfluidics device of claim 1, comprising a non-uniform electric field;
   (b) introducing a fluid solution comprising at least one particle into the microfluidics device; and
   (c) measuring a change in current or impedance using a field effect transistor at a time point selected from the group consisting of real-time, during or after the at least one particle influenced by the non-uniform electric field (i) enters a dielectrophoretic depletion zone, (ii) is immobilized in a dielectrophoretic high field region or low field region or (iii) is released in the dielectrophoretic high field region or low field region, respectively.

15. The method of claim 14, wherein the fluid solution has a conductivity ranging from about 0 S/m to about 5 S/m.

16. The method of claim 14, wherein the fluid solution has a viscosity of about 1 cP to about 100 cP or from about 0.0001 Pascal second to about 0.1 Pascal second.

17. The method of claim 14, wherein the microelectrode array device is capable of influencing particles ranging, in diameter, from about 10 nm to about 50,000 nm.

* * * * *